United States Patent
Hermann et al.

Patent Number: 5,843,031
Date of Patent: Dec. 1, 1998

[54] LARGE-DIAMETER INTRODUCER SHEATH HAVING HEMOSTASIS VALVE AND REMOVABLE STEERING MECHANISM

[75] Inventors: George D. Hermann, Los Gatos; Kirsten Freislinger, Menlo Park; Steven W. Kim, Cupertino; Jay A. Lenker, Laguna Beach; Michael A. Evans, Palo Alto, all of Calif.

[73] Assignee: Medtronic, Inc., Minneapolis, Minn.

[21] Appl. No.: 735,401

[22] Filed: Oct. 21, 1996

Related U.S. Application Data

[62] Division of Ser. No. 330,140, Oct. 24, 1994, Pat. No. 5,599,305.

[51] Int. Cl.$^6$ .................................................. A61M 37/00
[52] U.S. Cl. ........................... 604/95; 604/164; 604/167; 604/53; 604/200; 604/169; 604/170
[58] Field of Search .............................. 604/95, 164, 167, 604/53, 200, 169, 170, 264; 251/149.2, 149.6, 149.1, 149.4, 149.5, 149.11

[56] References Cited

U.S. PATENT DOCUMENTS

| | | | |
|---|---|---|---|
| 3,941,119 | 3/1976 | Corrales | 128/2 M |
| 4,066,070 | 1/1978 | Utsugi | 128/4 |
| 4,177,814 | 12/1979 | Knepshield et al. | 128/348 |
| 4,411,655 | 10/1983 | Schreck | 604/165 |
| 4,475,548 | 10/1984 | Muto | 128/207 |
| 4,586,923 | 5/1986 | Gould et al. | 604/95 |
| 4,610,674 | 9/1986 | Suzuki et al. | 604/282 |
| 4,634,432 | 1/1987 | Kocak | 604/167 |
| 4,643,194 | 2/1987 | Fogarty et al. | 128/668 |
| 4,976,688 | 12/1990 | Rosenblum | 604/95 |
| 4,983,165 | 1/1991 | Loiterman | 604/95 |
| 4,985,022 | 1/1991 | Fearnot et al. | 604/282 |
| 5,019,040 | 5/1991 | Itaoka et al. | 604/95 |
| 5,066,285 | 11/1991 | Hillstead | 604/164 |
| 5,069,217 | 12/1991 | Fleischhacker, Jr. | 128/657 |
| 5,098,412 | 3/1992 | Shiu | 604/280 |
| 5,104,389 | 4/1992 | Deem et al. | 604/264 |
| 5,109,830 | 5/1992 | Cho | 128/4 |
| 5,127,626 | 7/1992 | Hilal et al. | 251/149.1 |
| 5,167,636 | 12/1992 | Clement | 604/167 |
| 5,180,376 | 1/1993 | Fischell | 604/282 |
| 5,207,656 | 5/1993 | Kranys | 604/256 |
| 5,215,537 | 6/1993 | Lynn et al. | 604/244 |
| 5,221,255 | 6/1993 | Mahurkar et al. | 604/43 |

(List continued on next page.)

FOREIGN PATENT DOCUMENTS

| | | |
|---|---|---|
| 0 422 194 A2 | 10/1990 | European Pat. Off. . |
| 0 488 322 A1 | 6/1992 | European Pat. Off. . |
| 0 596 172 A2 | 12/1992 | European Pat. Off. . |
| 0 567 141 | 10/1993 | European Pat. Off. . |
| 3920-707-A | 1/1991 | Germany . |
| WO 94/01169 | 1/1994 | WIPO . |
| WO 94/11057 | 5/1994 | WIPO . |
| WO 94/21165 | 9/1994 | WIPO . |
| WO 96/13228 | 5/1996 | WIPO . |

OTHER PUBLICATIONS

Product label; Arrow International, Inc., Reading, Pennsylvania 19605; super Arrow Flex™.

*Primary Examiner*—Wynn Wood Coggins
*Assistant Examiner*—N. Kent Gring
*Attorney, Agent, or Firm*—Townsend and Townsend and Crew LLp

[57] ABSTRACT

A catheter introducing system includes an introducer catheter comprising a flexible sheath having a hemostasis valve and an obturator having a steering mechanism operated by a proximal actuator handle. The catheter introducer system will usually be introduced with the obturator inside of the flexible sheath so that the obturator can effect steering by laterally deflecting the distal end of the combined sheath and obturator. Such catheter introducing systems are particularly useful for large diameter sheaths which are not readily introduced over guide wires. A first exemplary hemostasis valve comprises a compressed foam insert having an axial lumen therein. A second exemplary hemostasis valve comprises an elastomeric insert which receives and seals over the catheter.

24 Claims, 13 Drawing Sheets

U.S. PATENT DOCUMENTS

| | | | |
|---|---|---|---|
| 5,221,270 | 6/1993 | Parker | 604/282 |
| 5,222,948 | 6/1993 | Austin et al. | 604/213 |
| 5,226,899 | 7/1993 | Lee et al. | 604/282 |
| 5,242,425 | 9/1993 | White et al. | 604/256 |
| 5,273,546 | 12/1993 | McLaughlin et al. | 604/167 |
| 5,275,152 | 1/1994 | Krauter et al. | 128/4 |
| 5,279,596 | 1/1994 | Castaneda et al. | 604/282 |
| 5,279,597 | 1/1994 | Dassa et al. | 604/283 |
| 5,284,474 | 2/1994 | Adair | 604/164 |
| 5,300,034 | 4/1994 | Behnke et al. | 604/167 |
| 5,334,185 | 8/1994 | Giesy et al. | 604/164 |
| 5,338,313 | 8/1994 | Mollenauer et al. | 604/209 |
| 5,380,304 | 1/1995 | Parker | 604/282 |
| 5,383,852 | 1/1995 | Stevens-Wright | 604/95 |
| 5,462,527 | 10/1995 | Stevens-Wright et al. | 604/95 |
| 5,467,763 | 11/1995 | McMahon et al. | 600/201 |
| 5,484,425 | 1/1996 | Fischell et al. | 604/282 |

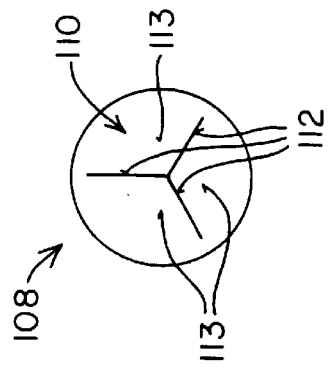
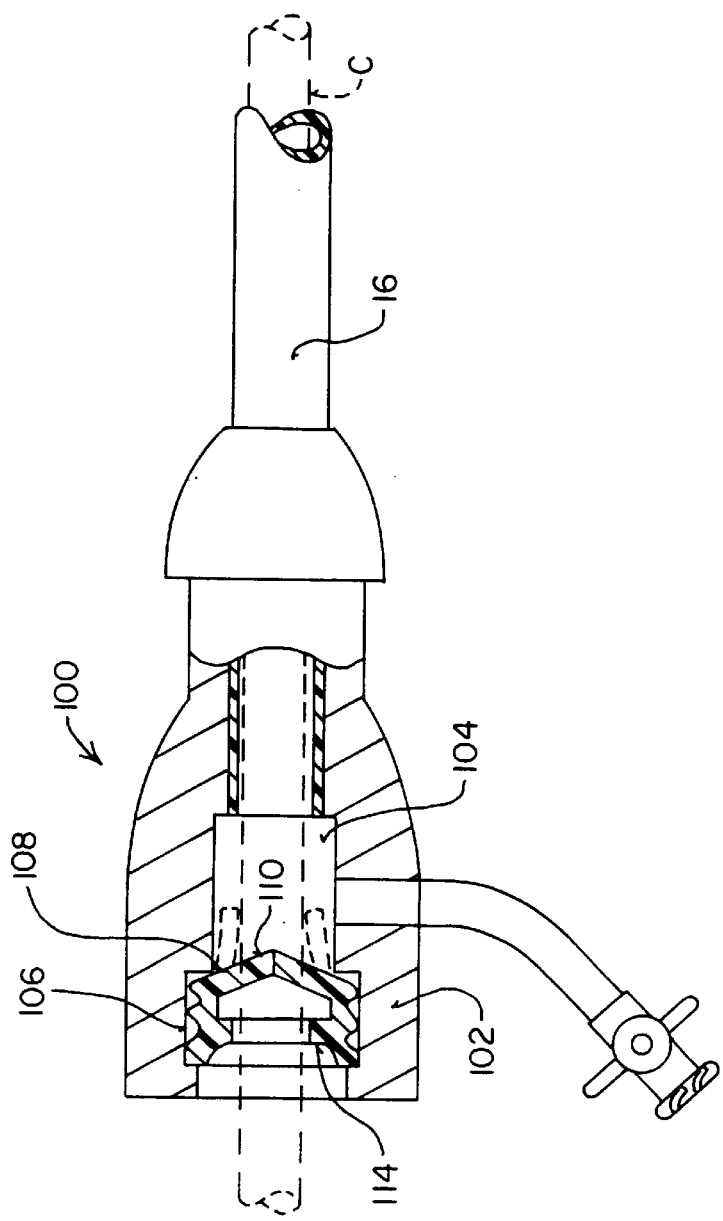
FIG. 13
FIG. 12

LARGE-DIAMETER INTRODUCER SHEATH HAVING HEMOSTASIS VALVE AND REMOVABLE STEERING MECHANISM

This is a Division of application Ser. No. 08/330,140 filed Oct. 24, 1994 now U.S. Pat. No. 5,599,305, the disclosure of which is incorporated by reference.

BACKGROUND OF THE INVENTION

Field of the Invention

The present invention relates generally to apparatus and methods for introducing devices to target locations within body lumens and cavities. In particular, the present invention relates to introducing catheters and methods which are used to provide large-diameter access lumens to target locations disposed along or at the distal end of tortuous paths.

Introducer sheaths and catheters are commonly used to provide endoluminal and/or percutaneous access to remote target locations in a variety of medical procedures, including intravascular procedures, laparoscopic procedures, and other minimally invasive procedures. Of specific interest to the present invention, the endovascular placement of vascular grafts for the treatment of abdominal aortic aneurysms has been proposed, where the graft may be inserted into the aorta via an antegrade or retrograde arterial approach. Such endovascular graft placement will require the use of a relatively large graft placement catheter, typically having an outer diameter in the range from 4 mm to 10 mm. Such large placement catheters will require correspondingly large introducing catheters or sheaths, typically having an internal lumen diameter which is at least slightly larger than the outer diameter of the placement catheter. The placement and use of such large-diameter introducing catheters or sheaths will be problematic in several respects.

In particular, the antegrade path into the subclavian artery, through the aortic arch, and into the thoracic aorta is quite tortuous. While the path can be readily negotiated by conventional intravascular guide wires, such guide wires have very small diameters and are not sufficiently strong to permit introduction of a large diameter introducing sheaths thereover. To overcome this problem, it would be possible to employ an introducing sheath having an integral steering mechanism. Such sheaths could be introduced around even the very tight curves encountered in the transition from the subclavian artery to the aortic arch. The incorporation of a steering mechanism, however, necessarily reduces the lumen area of the sheath which is ultimately available for accommodating the graft-placement catheter.

Other problems which arise when introducing sheaths are used for aortic access include the design of the hemostasis valve. The hemostasis valve must be able to accommodate very small devices, such as guide wires, as well as the very large graft-placement catheter. The body of the sheath must have a very thin wall (to maximize available area in the access lumen), and a very smooth lumen to permit the passage of the graft-placement catheters without sticking or constriction of the catheter. Additionally, placement of vascular grafts through an introducing sheath located in the abdominal aorta is further made difficult by the relatively high blood flow rate through the aorta. Moreover, the ability to anchor the vascular graft within the aorta and/or adjoining iliac arteries can be problematic and require additional devices which are difficult to provide through the limited area of the access lumen.

For these reasons, it would be desirable to provide improved catheter introducing systems and methods, including catheter sheaths, sheath steering mechanisms, hemostasis valves, and the like, which overcome at least some of the deficiencies described above. The introducing sheaths should have a large lumen diameter, typically being at least 4 mm, to accommodate large diameter graft-placement catheters, should have good hoop strength to avoid kinking or collapse of the sheath when bent around tight curves, and should have good column and tensile strengths to avoid deformation when the graft-placement catheter is passed through the lumen. The sheath steering mechanisms should provide for a high degree of lateral deflection at the distal end of the sheath but should not take up lumen area which is necessary for subsequent passage of large diameter catheters. The hemostasis valves should be able to accommodate both small diameter devices, such as guide wires, and the large diameter catheters while still maintaining a tight seal around the catheter to prevent leakage.

Description of the Background Art

A steerable sleeve for use in combination with a flexible catheter is described in DE 39 20 707. U.S. Pat. No. 4,976,688 shows a steerable sheath structure. European Patent Application 488 322 shows a tubular device having a variable curvature controlled by differential pressure. Other catheter- and device-steering mechanisms are described in U.S. Pat. Nos. 5,109,830; 5,098,412; 5,019,040; 4,983,165; 4,066,070; and 3,941,119.

A large-diameter introducer sheath having metal-ribbon reinforcement and a proximal hemostasis valve is described in U.S. Pat. No. 5,180,376. Devices covered by the '376 patent are sold by Arrow International, Inc., Reading, Pa. 19605, under the name super Arrow Flex™ percutaneous sheath introducer set with integral side port/hemostasis valve. Other reinforced tubular catheter designs are described in U.S. Pat. Nos. 5,279,596; 5 5,275,152; 5,226, 899; 5,221,270; 5,221,255; 5,069,217; 4,985,022; and 4,411, 655.

U.S. Pat. No. 5,207,656, discloses a hemostasis valve having a foam member for sealing against a catheter passed therethrough. The foam member has a lubricant absorbed in an open-cell foam structure. U.S. Pat. No. 4,475,548, discloses a foam sealing member for use in an endotracheal tube. European patent application 567,141 describes a trocar valve assembly which may include a flexibly resilient material for reception of an instrument passed through the valve. Other hemostasis and similar valve structures are described in U.S. Pat. Nos. 5,338,313; 5,300,034; 5,279,597; 5,242, 425; 5,222,948; 5,215,537; 5,167,636; 5,127,626; 5,104, 389; and 4,177,814.

SUMMARY OF THE INVENTION

The present invention provides apparatus and methods for placement of a flexible introducer sheath at a target location in a body lumen or cavity. Placement of the flexible sheath is usually percutaneous, i.e., through a puncture or incision in the patient's skin, and endoluminal i.e., through a body lumen or cavity which has been accessed through the percutaneous puncture site. An exemplary use of the apparatus and methods of the present invention is placement of a flexible sheath through the subclavian or brachial arteries, through the aortic arch, and into the abdominal aorta for the delivery of a vascular graft intended for treatment of an abdominal aneurysm. The apparatus and methods of the present invention, however, are not limited to use in such graft placement procedures and may find additional uses in a wide variety of procedures, including laparoscopic and other minimally invasive procedures where it is desired to introduce a large diameter sheath into a body cavity or lumen and subsequently steer or manipulate the distal end of the sheath to a target location within the luminal cavity.

In a first aspect of the present invention, a catheter introducing system comprises a flexible sheath having a proximal end, a distal end, and an access lumen extending therebetween. An obturator is removably received in the lumen of the flexible sheath and includes a mechanism for laterally deflecting at least a distal portion of the obturator. In this way, the distal end of the flexible sheath can be manipulated using the obturator to facilitate intravascular or other placement of the sheath. After the sheath has been introduced to the desired target location, the obturator may be withdrawn, leaving the access lumen open to receive guide wires, working catheters, and the like. Since the size of the obturator is limited only by the area of the sheath access lumen, there is sufficient available cross-sectional area for providing effective and efficient steering mechanisms. In particular, it will be possible to provide steering mechanisms which are capable of inducing small-radius deflections in the distal end of the sheath, typically as low as one cm.

In a second aspect of the present invention, a method for introducing a flexible sheath to a target location in a body lumen comprises introducing the sheath to the lumen and advancing the sheath within the lumen while laterally deflecting at least a distal portion of an obturator which is removably received in a lumen of the sheath. The obturator is removed from the sheath after the target location has been reached in order to provide the desired access lumen.

Usually, the obturator will be within the sheath with its deflectable distal end axially aligned with a distal portion of the sheath having enhanced flexibility. Alternatively, the obturator could be advanced distally beyond the sheath, using the steering mechanism to reach the desired target location, with the sheath then being advanced over the obturator. The method is particularly useful for introducing the sheath into the subclavian, external carotid, axillary, or brachial arteries, through the aortic arch, and into the abdominal aorta, but can also be used for a variety of procedures as described above.

In a third aspect of the present invention, an aortic introducer catheter comprises a flexible sheath having a proximal end, a distal end, and an access lumen extending therebetween. The length between the proximal and distal ends is in the range from 30 cm to 60 cm and the lumen diameter is in the range from 4 mm to 10 mm. A hemostasis valve is secured to the proximal end of the sheath, and the aortic introducer catheter is particularly useful for providing an access lumen into the subclavian or brachial arteries, through the aortic arch, and into the abdominal aorta. The catheter preferably has a region of enhanced flexibility over a distal length in the range from 5 cm to 15 cm so that it may be utilized in combination with a steerable obturator, as described above. The aortic introducer catheter may further comprise an expandable member, typically an inflatable balloon, located at from 1 cm to 10 cm from its distal end where the expandable member can be used to partially occlude blood flow when expanded inside the aorta. The catheter may additionally or alternatively, include an expandable member, again typically an inflatable balloon, at its distal end, where the distal expandable member can be used for anchoring an aortic prosthesis by internal expansion.

In a fourth aspect, the present invention provides a catheter sheath comprising a tubular inner liner having a proximal end, a distal end, and a lumen therebetween. The inner liner will preferably be formed from a lubricous material or have its inner lumen coated with a silicone gel or other lubricating material. Flat wire helical coil is wrapped over the exterior surface of the tubular inner liner, and the coil has spaced-apart adjacent turns. Plastic coating is formed over the helical coil and penetrates into the space between the adjacent turns. The coating bonds to the inner liner to provide an integral structure having a thin wall with controlled flexibility. The sheath preferably has a region of enhanced flexibility near its distal end, where flexibility can be controlled by utilizing liner materials, plastic coating materials, or both, having lower durometers near the distal end. Alternatively, the flexibility can be controlled by utilizing different helical coil materials or by modifying the spacing between adjacent coil turns to enhance the flexibility. The catheter sheaths will also preferably have a soft tip over a distal length in the range from 2 mm to 10 mm. The soft tip will usually be free from the helical coil and may optionally be formed from a material having a lower durometer.

In a fifth aspect of the present invention, a steerable obturator is provided comprising a flexible body having a proximal end and a tapered distal end. A mechanism will be provided in the body for laterally deflecting at least a distal portion of the body. Typically, the lateral deflection mechanism will comprise a pull wire which is attached off center at the distal end of the flexible body. The pull wire can be actuated by a handle secured to the proximal end of the body. The obturator will preferably have a region of enhanced flexibility at its distal length, where the region of enhanced flexibility may comprise a series of articulated elements.

In a sixth aspect, the present invention provides a hemostasis valve comprising a housing having an interior cavity and axially aligned inlet and outlet ports. A compressible insert is disposed within the interior cavity of the housing and includes a polymeric foam body having an open axial lumen in an exterior geometry which is similar to but larger than the interior cavity in the housing. By confining the foam insert within the interior cavity of the housing, the open lumen will be closed to provide a seal between the axial lined ports of the housing. The circumference of the lumen, however, will be sufficiently large to accommodate even large diameter catheters and devices subsequently introduced through the valve. The particular advantage of this design is that the lumen in the foam insert will not be stretched or torn as the catheter is being introduced therethrough. That is, the original cross-sectional circumference of the lumen will remain even though the lumen has been collapsed by external compression. Preferably, the hemostasis valve will include a second valve element, such as a duckbill or slit disc structure to provide for hemostasis when no catheter or device is placed through the foam insert. The lumen of the foam insert will also preferably be coated with a lubricant and optionally provided with a protective layer to further guard against tearing of the foam as the catheter is passed therethrough.

BRIEF DESCRIPTION OF THE DRAWINGS

FIG. 12 is a partial cross-sectional view of an alternative hemostasis valve which can be mounted at the proximal end of the flexible sheath of the catheter introducing system of FIG. 1.

FIG. 13 is a front view of an elastomeric insert included in the hemostasis valve of FIG. 12.

DESCRIPTION OF THE PREFERRED EMBODIMENT

Figure 1:
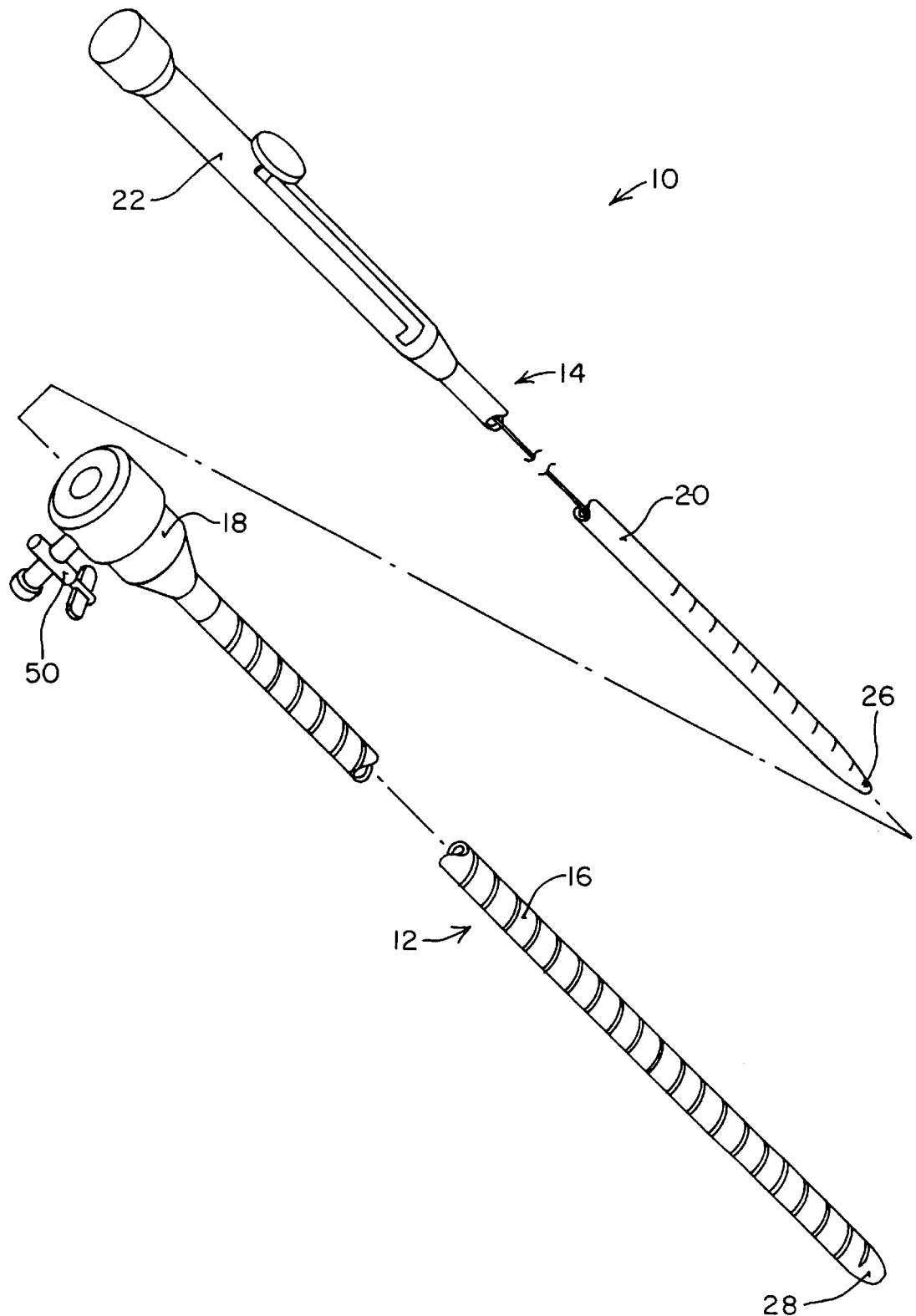
FIG. 1 is a prospective view of the catheter introducing system constructed in accordance with the principles of the present invention and including a flexible sheath and an obturator having a laterally deflectable distal end.

The present invention provides a catheter introducing system including both a large diameter sheath and a steerable obturator which can be removably introduced into a central lumen of the sheath. The sheath is usually part of an introducer catheter having a hemostasis valve at its proximal end. The sheath and obturator are usually introduced together through a percutaneous access site to a desired target location within a body lumen or cavity, with the steerable obturator being used to guide the sheath through a tortuous path such as in a blood vessel or within an open body cavity, such as in an insufflated abdomen during a laparoscopic procedure. Alternatively, the obturator could be advanced distally beyond the sheath, with the sheath being subsequently advanced over the obturator. In either case, the obturator is removed after the sheath reaches the target location, providing an open access lumen for subsequent introduction of interventional or other catheters and devices. The catheter introducing system of the present invention is particularly useful for introducing large diameter interventional catheters, especially into the brachial or subclavian arteries, through the aortic arch, and into the abdominal aorta, more especially for graft placement to treat abdominal aortic aneurysms.

The sheath of the catheter introducing system will preferably include only a single lumen having a relatively large diameter, usually being at least 4 mm, preferably being from 4 mm to 10 mm, and more preferably being from 5 mm to 9 mm. For use in the exemplary aortic introducing catheter, the sheath will have a lumen diameter from 7 mm to 8 mm, and an outer diameter from 8 mm to 9 mm. In order to maximize available lumen area (which is an objective of the design of the catheter introducing system), the sheath will have a thin wall, usually being from 0.25 mm to 1 mm. The sheath length will vary depending on the intended use, typically being from 30 cm to 60 cm. For use in the exemplary aortic introducer catheter, the sheath length will be from 40 cm to 60 cm, usually being from 40 cm to 50 cm.

The body of the flexible sheath must have sufficient hoop strength in order to avoid kinking and collapse during use, even when the sheath is bent through a small radius curve, preferably as small as about 1 cm. The sheath must also have sufficient column strength so that it can be advanced through restricted passages (although the obturator present in the sheath lumen will contribute significantly to its effective column strength). To meet these mechanical requirements, the sheath of the present invention will preferably be reinforced, such as by an imbedded metal coil, braid, filament(s), or the like. In a preferred aspect of the present invention, as illustrated in the exemplary embodiments below, the sheath will be reinforced with a helical coil formed from a flat metal ribbon, usually a stainless steel ribbon. The stainless steel ribbon preferably has a width in the range from about 0.5 mm to 1.5 mm and a thickness in the range from about 0.08 mm to 0.15 mm. In a particularly preferred construction, the ribbon is wrapped over an inner liner (as described below) having from 5 turns to 15 turns per centimeter, wherein the spacing between the adjacent turns is in the range from 0.5 mm to 1 mm.

In the exemplary embodiment, the inner liner may be formed from a lubricous material, such as polytetrafluoroethylene (PTFE), fluorinated ethylenepropylene polymer (FEP), polyether block amide copolymer (pebax), polyamide (nylon), polyethylene, and the like. The tubular inner liner will typically have a thickness in the range from about 0.08 mm to 0.15 mm. The inner liner may also be formed from a non-lubricous material, such as a polyurethane, where the inner lumen of the liner is coated with a lubricating material, such as a silicone gel. Optionally, the lubricating layer may also be used with other, more lubricous materials, in order to provide even greater lubricity for the introduction of instruments and devices through the sheath. The helical coil will be wrapped over the inner liner, and an outer plastic coating will be melted or otherwise impregnated over the coil and into the space between adjacent turns of the coil. The plastic coating is preferably composed of a material which has elastic properties similar to those of the liner. Suitable materials include polyurethane, polyethylene (pebax), polyamide (nylon), and the like. The thickness of the coating measured from the inner liner to the exterior of the sheath is typically in the range from 0.8 mm to 0.15 mm. In a preferred construction, both the inner liner and the outer plastic coating are composed of polyurethane, and the lumen of the combined inner and outer liner assembly is coated with a silicone, hydrophilic, or other lubricant. Such lubricating coatings are well described in the patent literature. See, for example, U.S. Pat. No. 4,898,591, which is incorporated herein by reference.

In a preferred aspect of the present invention, the flexible sheath will have regions of differing flexibility over its length, preferably having a region of enhanced flexibility over a distal length in the range from about 5 cm to 15 cm, more preferably from 5 cm to 10 cm. Such enhanced flexibility may be achieved by increasing the spacing between adjacent turns of the reinforcement coil (thus providing reduced reinforcement in the enhanced flexibility region), utilizing materials for the inner liner and/or outer plastic coating having lower durometers, selectively reducing wall thickness, or by other conventional techniques.

The flexible sheath of the catheter introducing system will also preferably have a soft tip formed over the distal 2 mm to 10 mm of the sheath body. The soft tip may be formed by terminating the reinforcement in the soft tip region. Additionally or alternatively, the softness of the tip can be enhanced by utilizing the same or different materials for the inner liner and/or outer coating, where the materials have a lower durometer in the soft tip region.

The flexible catheter sheath of the catheter introducing system may be fabricated by methods well known in the art. In an exemplary method, the inner layer is formed by wrapping a strip of the desired plastic material, e.g., a polyurethane, over a mandril, typically a teflon rod having the desired final inner lumen diameter. A stainless steel reinforcement ribbon is next wrapped helically over the polyurethane. Next, another strip of the desired plastic coating material, e.g., polyurethane, is wrapped over the stainless steel reinforcement. A shrink wrap tube may then be placed over the entire assembly, and the assembly cured in an oven at a temperature sufficient to melt both the inner layer material and outer layer plastic coating material and to cause shrinkage of the shrink tube to apply compressive pressure. The shrink tube is then removed and the flexible sheath cut to the desired length. Optionally, a silicone, hydrophilic, or other lubricant is then coated over the interior surface of the sheath lumen to facilitate introduction and withdrawal of instruments and devices though the sheath. Such a manufacture results in a generally tapered distal end of the flexible sheath when the metal reinforcement band is terminated at the desired distance from the distal tip.

The introducer catheter of the present invention will include a hemostasis valve secured to the proximal end of the sheath. A wide variety of hemostasis valves would be suitable, including the valves described in U.S. Pat. Nos. 5,338,313; 5,300,034; 5,279,597; 5,242,425; 5,222,948; 5,317,537; 5,207,656; 5,127,626; 5,109,389; and 4,177,814, the full disclosures of which are incorporated herein by reference. The introducer catheter of the present invention, however, preferably employs a hemostasis valve construction which provides for tight lateral sealing against catheters having a wide range of outside diameters, e.g., from guide wires to catheters as large as 30 French (10 mm; one French (F) equals 0.33 mm), often as large as 26 F, and preferably as large as 22 F.

A first exemplary hemostasis valve construction employs a foam insert having an axial lumen. The foam can be an open cell foam, a closed cell foam, or combination thereof. Suitable foam materials include silicones, polyurethanes, polyethylenes, and the like. The foam insert will be contained within a housing having an interior cavity with axially aligned inlet and outlet ports. The foam insert will be oversized, with the axial lumen being open when the insert is an uncompressed state. Usually, the open diameter of the lumen is at least 0.5 mm, preferably being in the range form 0.5 mm to 5 mm. When the foam insert is disposed within the interior housing of the cavity, however, the insert will be compressed sufficiently to close the lumen. The resilient nature of the foam will permit the lumen to reopen as the catheter is advanced therethrough. Since the original periphery of the lumen is maintained (albeit compressed), even large catheters up to the original diameter of the lumen (or even slightly larger) will be able to reopen the lumen without tearing or overextending the lumen.

In a particular aspect of the first exemplary hemostasis valve, a second valve element will be provided in series with the foam insert. Typically, the second element will be a duck bill or slit valve structure intended to close the hemostasis valve when no catheter is present in the valve. The lumen of the foam insert may also be covered with a protective layer and/or coated with a lubricant. The protective layer will be composed of a material which is sufficiently flexible to open and close with expansion of the lumen but which is sufficiently tough to further protect against tearing or disintegration of the foam insert, preferably being a polyurethane, a silicone, polyvinyl alcohol, or the like.

An alternative hemostasis valve construction employs an elastomeric insert contained within a housing having an interior cavity with axially aligned inlet and outlet ports. The elastomeric insert has a generally cylindrical shank with a forwardly disposed conical face. The conical face is radially split to form at least three "petals" which will open as catheters pass therethrough. Pressure downstream of the valve will hold the conical face closed when no catheter is present. Optionally, the elastomeric insert may include an annular ring disposed proximally of the forward conical face. The annular ring will provide structural support (hoop strength) for the insert and may provide a sliding seal against catheters which pass therethrough.

The flexible sheath of the present invention may further include a first expandable member, typically an inflatable balloon, located at from 1 cm to 10 cm from the distal end of the sheath. The balloon is located on the exterior of the sheath body and intended to at least partially occlude blood flow when the sheath is present in a blood vessel, usually the aorta when the sheath is part of an aortic introducer catheter. A second expandable member may also or alternatively be disposed near the distal end of the sheath in order to anchor the sheath at a desired location. Particular use of the distal expandable member, which will also typically be a balloon, is to internally expand a vascular prosthesis, such as a vascular graft, in procedures such as the placement of vascular grafts in order to treat abdominal aortic aneurysms.

The steerable obturator which forms part of the catheter introducing system comprises a flexible body having a proximal end and a distal tip. The distal tip will usually be closed, typically being tapered or blunt. The mechanism for laterally deflecting at least a distal portion of the flexible body provides the desired steering capability. The obturator will typically have a length which is at least equal to that of the flexible sheath so that the laterally deflectable (steerable) distal end of the obturator can be aligned with the distal, enhanced flexibility region of the sheath. In this way, when the obturator is present within the sheath, the obturator can be used to steer the sheath to desired target locations as will be described in more detail below. In some cases, it may be desirable to provide obturator having lengths substantially greater than that of the associated flexible sheath which is part of the catheter introducing system. In those cases, it will be possible to advance the obturator beyond the distal end of the sheath and subsequently advanced the sheath over the obturator, after the obturator has reached desired target location. Thus, the length of the obturator will typically be in the range from 50 cm to 75 cm, preferably being from 45 cm to 60 when it is intended to match the sheath length.

The diameter of the flexible body of the obturator will usually be slightly less than that of the lumen diameter of the flexible sheath, typically being about 0.5 mm to 1 mm less than the lumen diameter. Such a close tolerance is desirable since it assures that the flexible sheath will conform closely to the obturator which in turn facilitates steering of the sheath using the obturator.

The flexible body of the obturator can be formed from a variety of materials, typically being a polymer such as polyurethane, pebax, nylon, or other thermoplastic elastomer. Usually, the distal portion of the obturator which is intended to be laterally deflected, i.e., steered, will have a substantially greater flexibility than the proximal portions of the obturator. The length of the enhanced flexibility (steerable) region of the obturator will usually correspond to that of the enhanced flexibility distal portion of the sheath, typically being from 5 cm to 15 cm, preferably from 5 cm to 10 cm. Such flexibility can be enhanced by appropriately choosing the material of the distal portion, the durometer of the distal portion, and optionally by mechanically modifying the body to have enhanced flexibility. For example, the body may include a series of partial cuts along the side which will be expected to have the greater radius when the distal end is laterally deflected.

Alternatively, and in some cases preferably, the enhanced flexibility distal portion of the obturator may be formed as a plurality of articulated members, such as pivotally attached links. An internal spring may be disposed within the links in order to provide a desired counter force against the lateral deflection mechanism, as described in more detail below. Each link will typically have a length from 0.5 cm to 1.5 cm with a total number of links from 3 to 6. Individual links can be formed from any medically acceptable material having sufficient strength and rigidity, such as stainless steel, polycarbonate, glass-reinforced acetyl resin thermoplastic (such as Delrin®), and the like.

A variety of catheter steering mechanisms are known in the art which can be employed in the obturator of the present invention. Usually, lateral deflection in only a single direction will be provided. The obturator and flexible sheath may then be rotated about their respective axes in order to direct the combination in the desired direction. Such a steering mechanism can be readily fabricated using a single pull wire which is connected off center at the distal end of the obturator.

The steering mechanism will further include an actuating handle at the proximal end of the flexible obturator body. In the case of a single pull wire steering mechanism, the actuator handle will include a first element attached to the flexible body and a second element attached to the pull wire. By properly translating the first and second elements relative to each other, the desired lateral deflection can be induced in the distal tip of the obturator.

Figure 2:
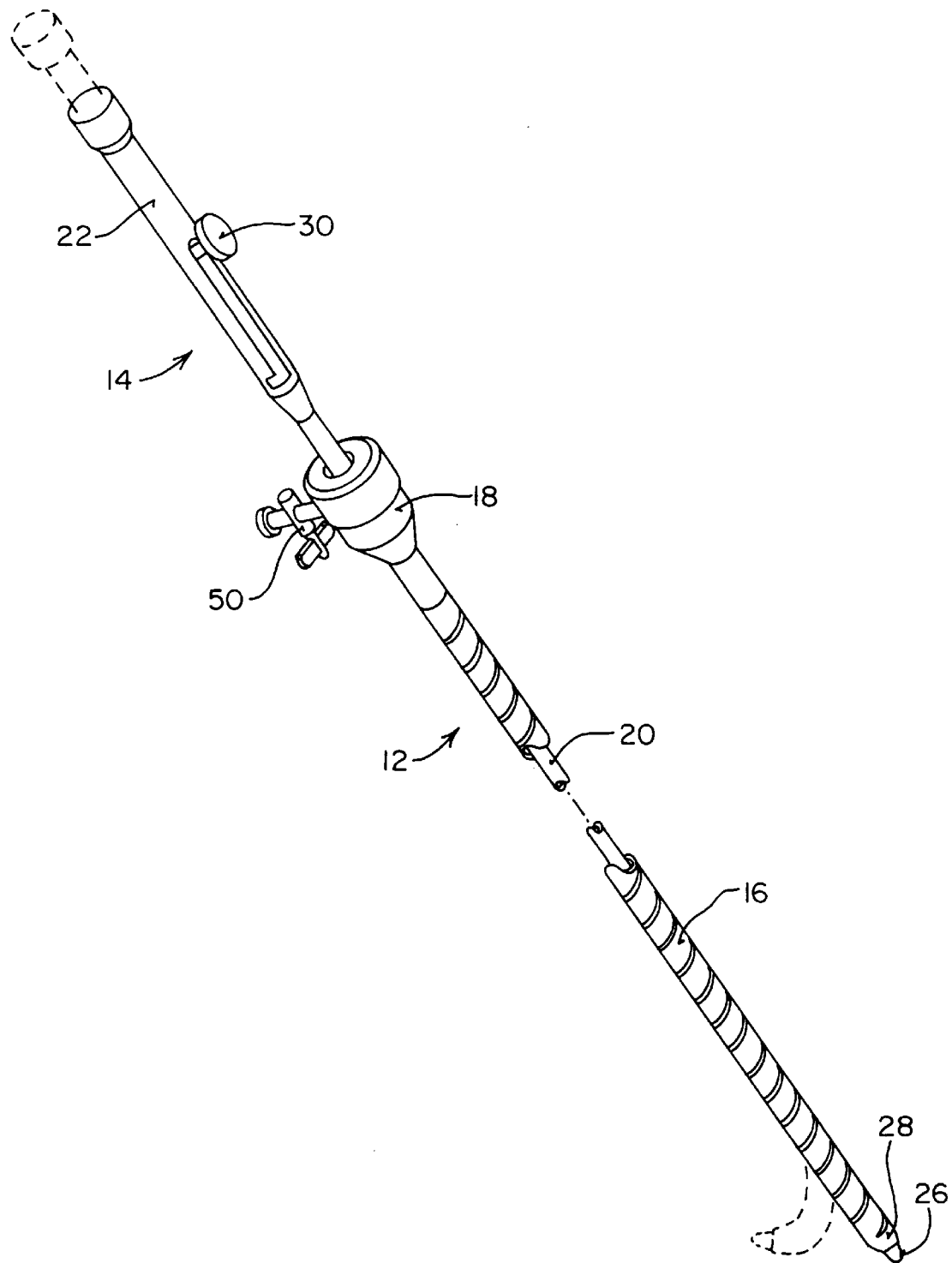
FIG. 2 is a prospective view of the catheter introducing system of FIG. 1, shown with the obturator located in an axial lumen of the flexible sheath, with a laterally deflected distal end shown in broken line.

Referring now to FIGS. 1–5, a catheter introducing system 10 constructed in accordance with the principles of the present invention includes an introducing catheter 12 and an obturator 14. The introducing catheter 12 in turn comprises a flexible sheath 16 and a hemostasis valve assembly 18. The obturator 14 includes both a flexible body portion 20 and an actuator handle 22. As illustrated in FIG. 1, the obturator is withdrawn from the central lumen 24 (FIG. 5) of the flexible sheath 16. FIG. 2 illustrates the obturator 14 in place within the introducer catheter 12 with a tapered distal tip 26 extending from the distal end 28 of the sheath 16. As will be described in greater detail below, proximal retraction of actuator handle 22 relative to thumb lever 30 causes lateral deflection of a distal portion of both the obturator 14 and the flexible sheath 16 which is disposed over the obturator. Preferably, at least the flexible sheath will have enhanced flexibility over the region which is laterally deflected.

Figure 3:
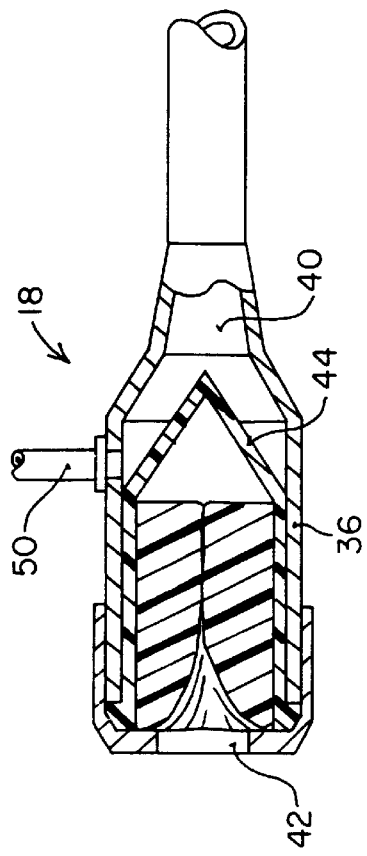
FIG. 3 is a partial cross-sectional view of a hemostasis valve mounted at the proximal end of the flexible sheath of the catheter introducing system of FIG. 1.
Figure 4:
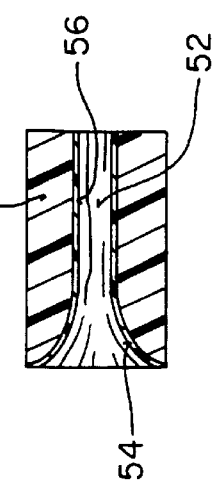
FIG. 4 is a cross-sectional view of a foam insert included in the hemostasis valve of FIG. 3.

As best shown in FIG. 3, hemostasis valve assembly 18 comprises a housing 36 having a foam insert 38 disposed therein. The housing defines axially aligned inlet and outlet ports 40 and 42, respectively for receiving a guide wire, interventional catheter, or other elongate device therethrough. The valve further includes a duck bill structure 44 for sealing against pressure through inlet port 40 when no catheter or other device is disposed in the hemostasis valve. A perfusion connector 50 (best illustrated in FIGS. 1 and 2) is mounted on the housing and communicates with the inlet port 40 upstream of the duck bill 50. Thus, fluid access to the lumen 24 may be maintained regardless of whether a catheter is present in the hemostasis valve assembly 18.

In preferred aspect of the present invention, the foam insert 38, in its uncompressed configuration (FIG. 4), will have an open axial lumen 52, more preferably being flared open at its proximal end 54. The lumen 52 will close, however, when the insert 38 is confined within the housing 36, as illustrated in FIG. 3. As discussed above, the inherently large cross-sectional area of the lumen 52 is advantageous since it permits the lumen to receive relatively large catheters and other working devices without stretching or damaging the foam insert. In a particularly preferred aspect, a protective coating layer 56 will be formed over the lumen 52 surface in order to further protect against damage and loss of material.

Figure 5:
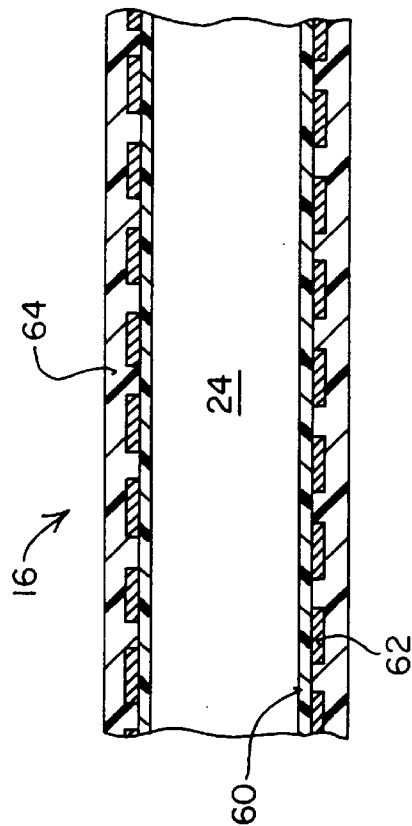
FIG. 5 is a partial cross-sectional view of the body of the flexible sheath of the catheter introducing system of FIG. 1.

Referring now to FIG. 5, the flexible sheath 16 comprises an inner lubricous liner 60 having a helical metal coil 62 wrapped over its exterior surface. An outer plastic coating 64 is then formed over the exterior surface of the liner as well as the metal coil. Specific materials and methods for forming this structure are described above.

Figure 6:
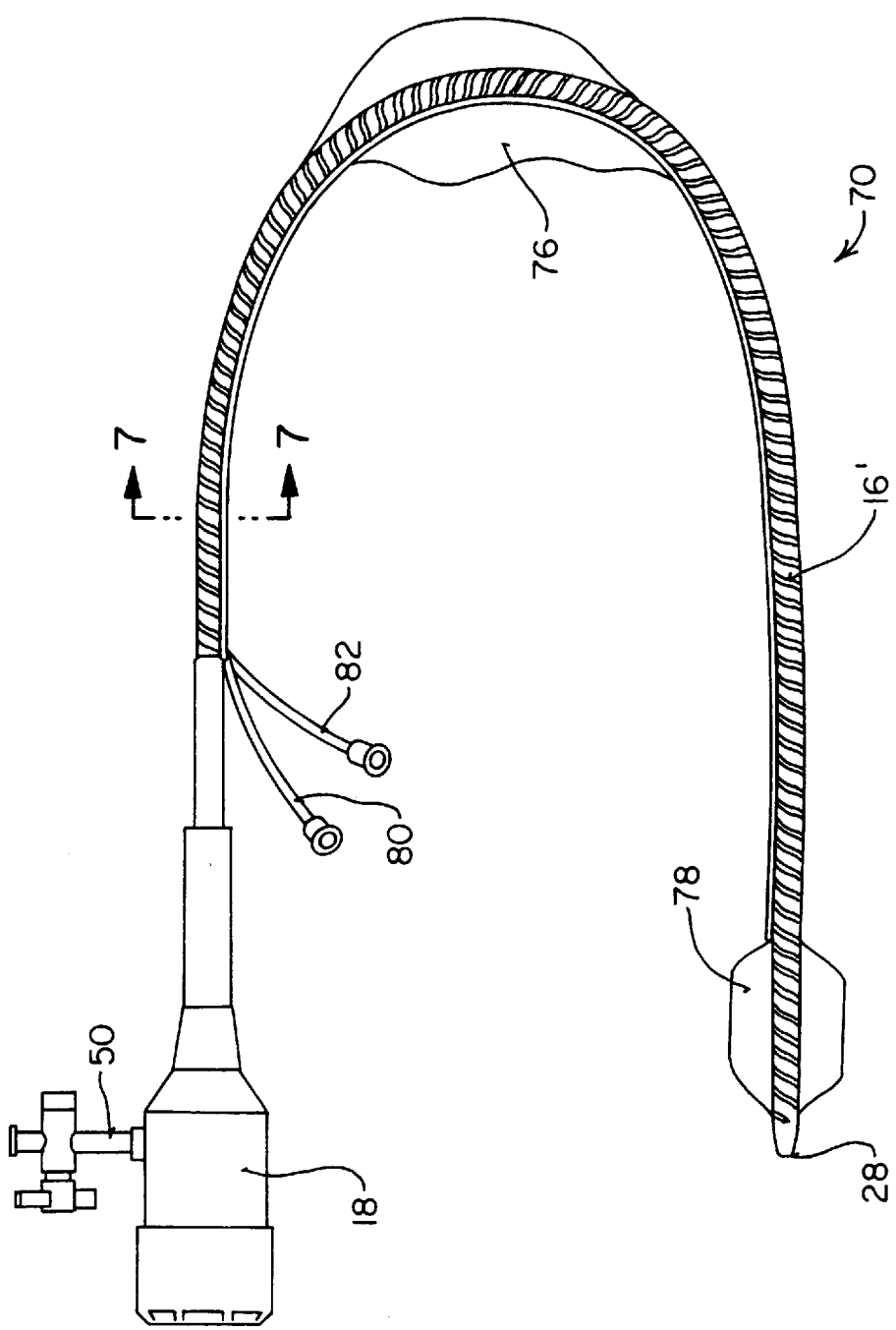
FIG. 6 is a side view of an alternate construction of the flexible sheath of the catheter introducing system of the present invention.
Figure 7:
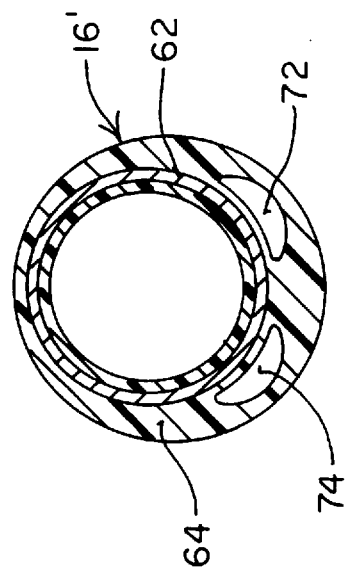
FIG. 7 is a cross-sectional view taken along line 7—7 of FIG. 6.
Figure 8:
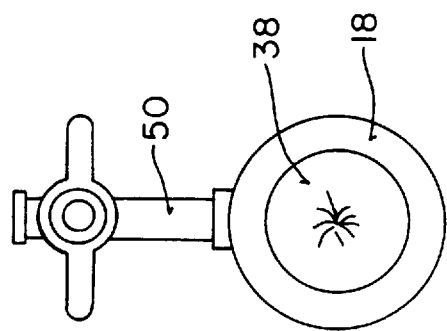
FIG. 8 is a proximal end view of a hemostasis valve on the flexible sheath of FIG. 6.

Referring now to FIG. 6, an aortic introducer catheter 70 particularly intended for introducing devices into the brachial or subclavian arteries, through the aortic arch, and into the abdominal aorta is illustrated. The introducer catheter 70 is constructed generally the same as that shown in FIGS. 1 and 2, with identical components given identical numbers. The flexible sheath 16', however, is provided with a pair of inflation lumens 72 and 74, as illustrated in FIG. 7. The inflation lumens 72 and 74 are connected to a first inflatable balloon 76 and a second (distal) inflatable balloon 78. The first balloon will generally have a diameter, when inflated, in the range from about 10 mm to 30 mm. The purpose of the first balloon 76 will be to provide partial occlusion of blood flow when present in the abdominal aorta. The diameter of the second balloon 78 will typically be from 15 mm to 22 mm when inflated. The purpose of the second balloon 78 will be to anchor the distal end of the catheter and, in a more particular aspect, to anchor expandable grafts and other prostheses within the aorta according to the method described hereinafter. The balloons may be formed from a non-distendable material which allows for precise control of the expanded diameter. Alternatively, either or both balloons could be formed from elastomeric materials to permit expansion over a wide range of aorta sizes. The formation of such expandable balloons is well described in the art. Lumen connectors 80 and 82 will be provided in order to connect the balloons to suitable inflation sources, typically pressurized contrast medium. An end view of housing 18 is shown in FIG. 8.

Figure 9:
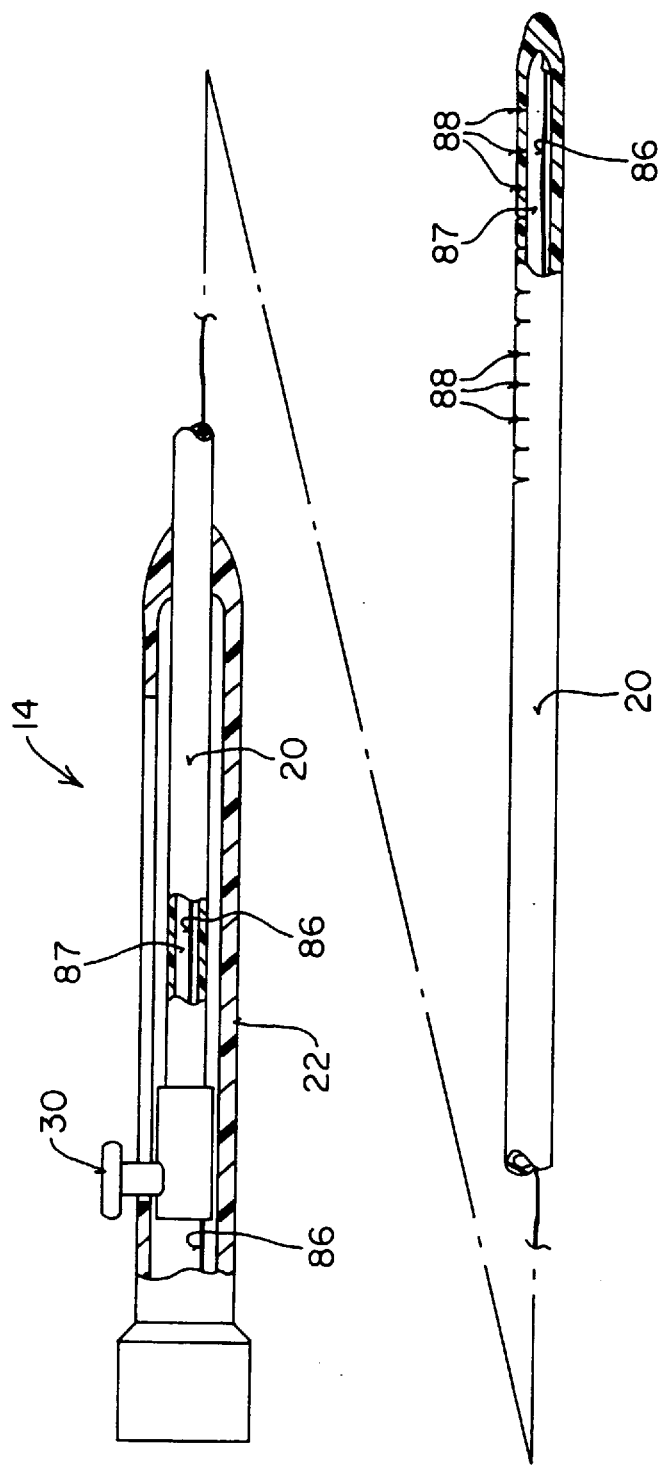
FIG. 9 is a side view of the obturator of the catheter introducing system of FIG. 1 shown with portions broken away.

Obturator 14 is illustrated in more detail in FIG. 9. Thumb lever 30 of the actuator handle 22 is slidably mounted within the handle and connected to the proximal end of flexible body 20. Flexible body 20 is tubular, typically having a closed distal tip which is preferably tapered to provide atraumatic introduction to the desired target body location. A pull wire 86 is attached off center to the distal tip of the flexible body 20. The pull wire extends through a lumen 87 of the flexible body and is attached at the proximal end of the actuator handle 22. Thus, distal motion of the thumb lever 30 relative to the actuator handle 22 will cause the pull wire to shorten relative to the flexible body 20. Such shortening, in turn, will cause the distal tip to bend downward relative to the position shown in FIG. 9. Such downward deflection is enhanced by weakening of the opposite (upper) side of the flexible body over the portion which is desired to be laterally deflected. As illustrated in FIG. 9, a series of cuts 88 may be made partially through the flexible body portion 20 in order to provide the desired weakening.

Figure 10:
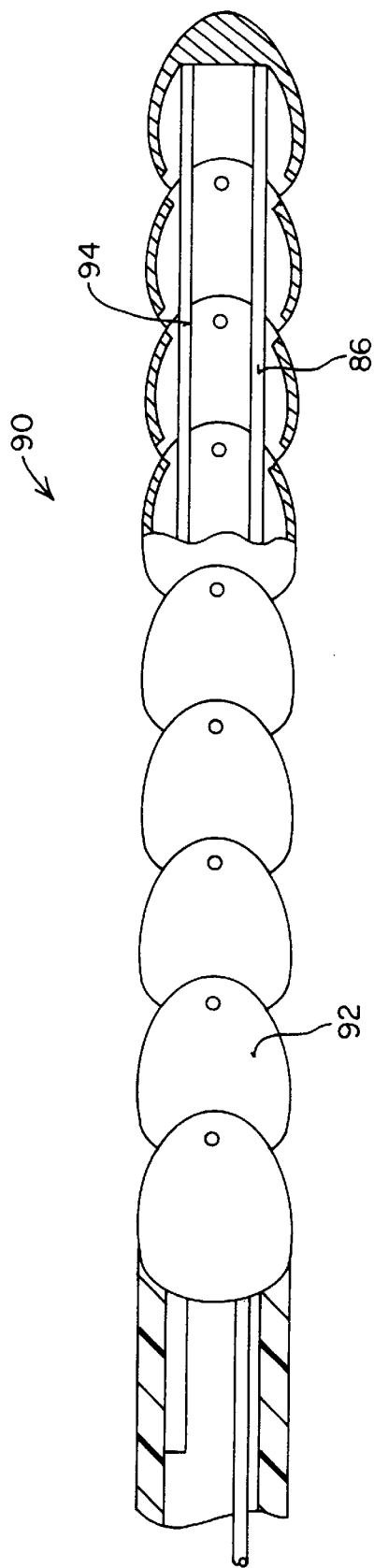
FIG. 10 illustrates an alternative construction of the laterally deflectable distal end of the obturator of FIG. 9.

Referring now to FIG. 10, an alternative construction for the deflectable distal end of obturator 14 is illustrated. Deflectable end 90 comprises a plurality of articulated links 92 which are pivotally connected. Pull wire 86 extends through the pivotally connected links 92, and a spring member 94, typically formed from nickel-titanium alloy or other super elastic material, is disposed opposite to the pull wire 86. The spring provides for straightening of the distal tip when no tension is placed on pull wire 86. The use of pivotally attached lengths 92 is desirable since it provides a highly flexible distal end for the obturator.

Referring now to FIGS. 11A–11E, use of the catheter introducer system 10 for placement of the flexible sheath 16 through the subclavian artery SC, across the aortic arch AA, and into the abdominal aorta ABA will be described. Such procedures are particularly useful for introducing straight or bifurcated grafts G (Fig. 11E) for the treatment of abdominal aneurysms A.

The catheter introducer system is initially introduced through an appropriate percutaneous access procedure so that the distal end of the system enters the target artery. Common percutaneous access procedures include the Seldinger technique, the use of arterial dialators, and the surgical exposure and isolation of the artery (commonly referred to as a "cut down" procedure). The catheter introducer system may be inserted via the brachial artery, the axillary artery, the subclavian artery, the femoral artery, or the popliteal artery using any of these percutaneous or surgical procedures. Alternatively, the introducer system can be placed into the iliac arteries by direct surgical exposure.

Figure 11A:
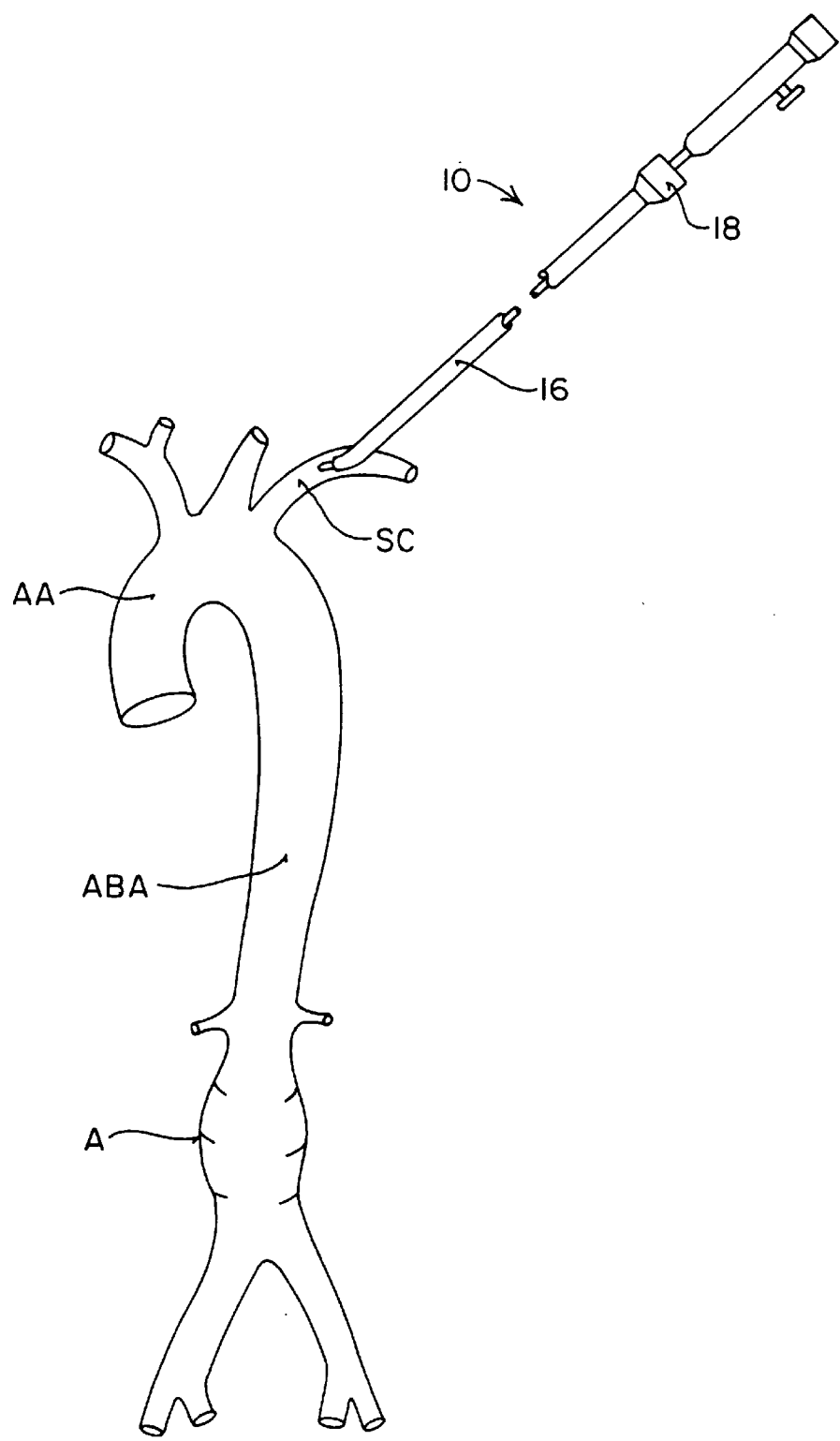
FIGS. 11A–11E illustrate use of the catheter introducing system of FIG. 1 for introducing a vascular graft through the subclavian artery, aortic arch, and abdominal aorta.
Figure 11B:
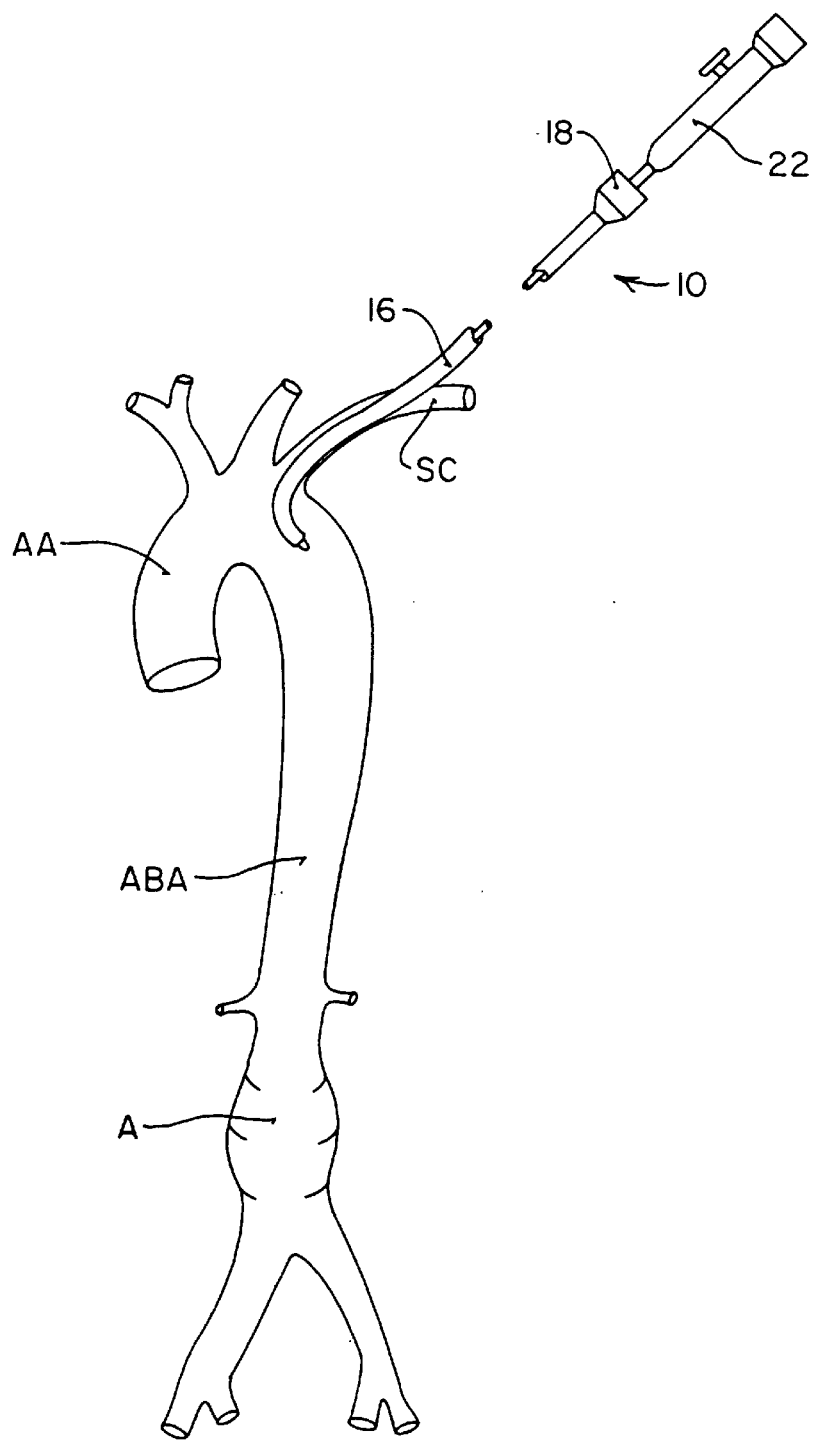
Figure 11C:
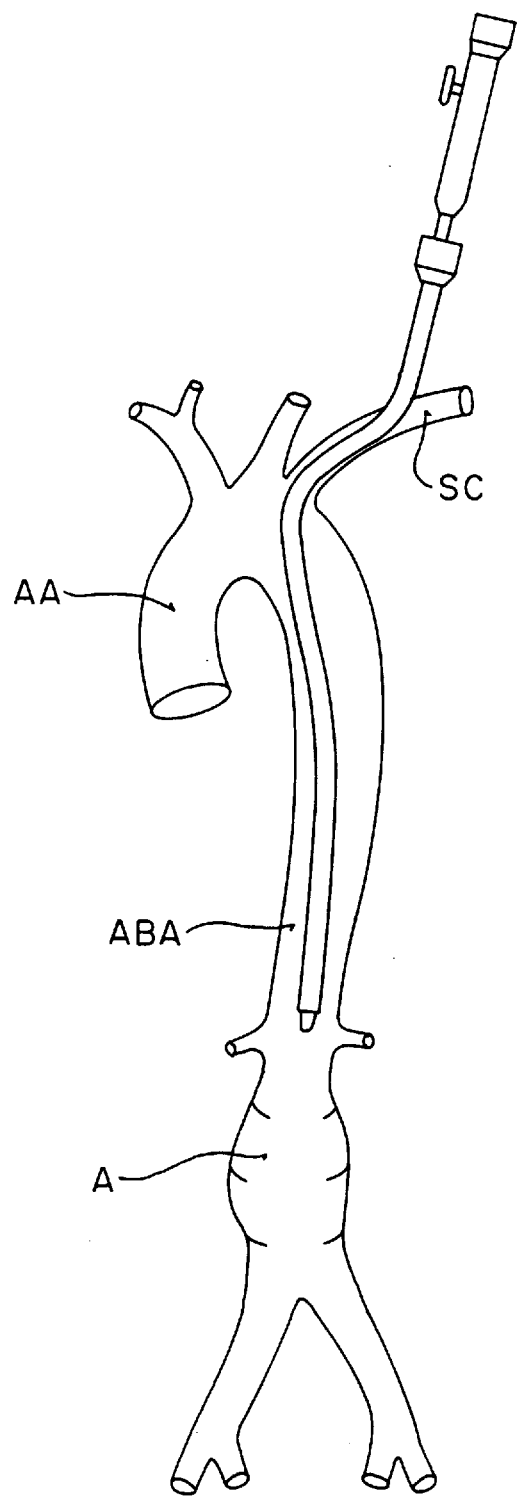
Figure 11D:
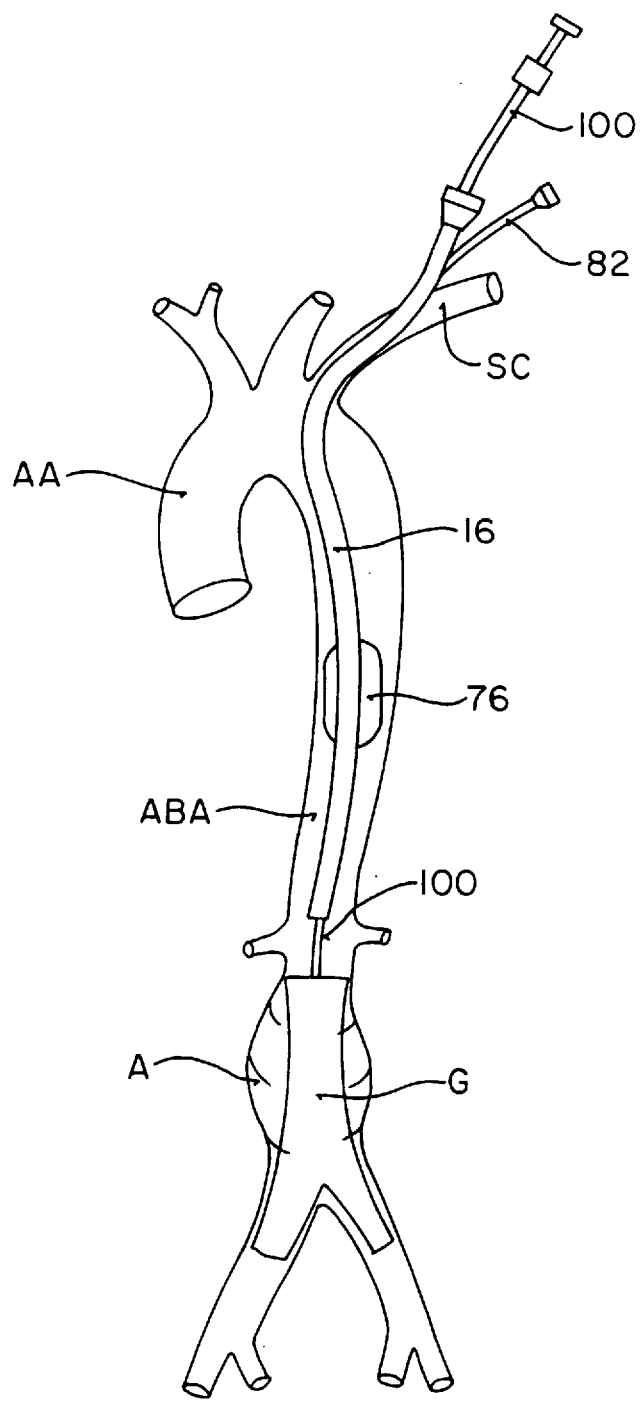
Figure 11E:
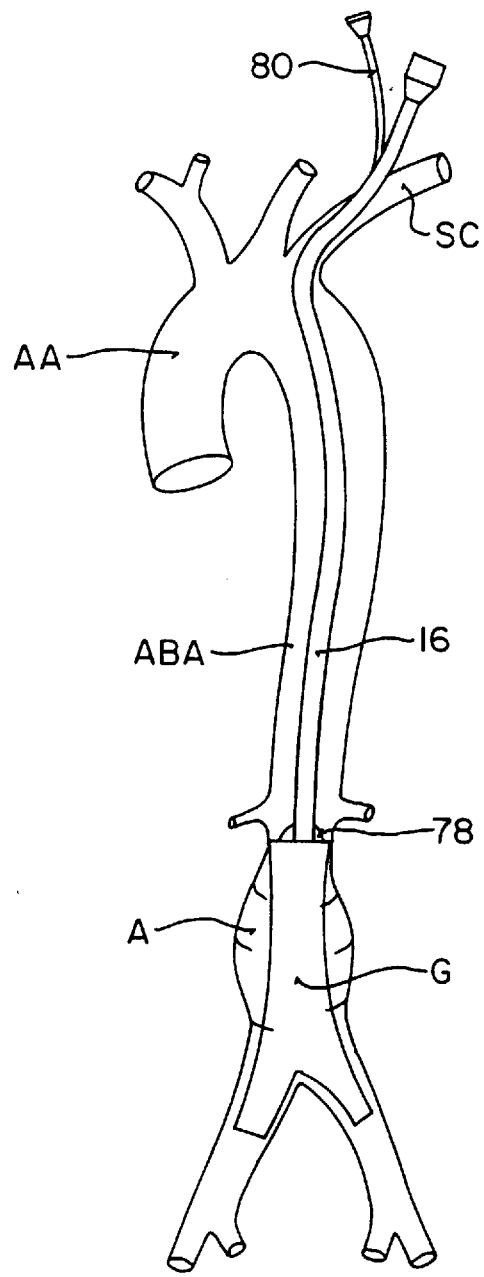

FIGS. 11A–11E illustrate the case of introducing the catheter system through the subclavian artery. The distal end can be deflected in a desired direction, as illustrated in FIG. 11A, so that it may pass down the subclavian artery SC toward the aortic arch AA. After reaching the aortic arch AA, as illustrated in Fig. 11B, the catheter introducer system 10 may be rotated about its axis and the tip deflected in the opposite direction to properly enter into the aortic arch AA. The introducer system 10 is then further advanced down the abdominal aorta ABA toward the aneurysm A, as illustrated in Fig. 11C, with the tip direction being manipulated by turning the handle and deflecting the tip in an appropriate manner.

After reaching the region of the abdominal aorta ABA just over the aneurysm A, the obturator 14 can be removed leaving an access lumen in sheath 16 to the abdominal aorta. A delivery catheter 100 can then be advanced through the sheath 16 in order to deliver graft G, in a manner generally described in copending applications Ser. Nos. 08/290,021, filed on Aug. 12, 1994, and 08/255,681 filed on June 8, 1994, the full disclosures of which are incorporated herein by reference. During placement of the graft G, the partial occlusion balloon 76 will preferably be expanded in order to slow blood flow to the region of the aneurysm A. Such a reduction in blood flow rate makes placement of the graft G substantially easier. Once in place, the graft G can be anchored by manipulating flexible sheath 16 so that distal balloon 78 enters the end of the graft G. Expansion of balloon 78 within the graft G helps to anchor the balloon against the aortic wall. The flexible sheath 16 may then be withdrawn from the aorta after proper placement of the graft G has been confirmed.

Referring now to FIGS. 12 and 13, an alternative hemostasis valve assembly 100 which may be used in place of valve assembly 18 will be described. Hemostasis valve assembly 100 is attached to the proximal end of flexible sheath 16 and comprises a valve body 102 having an internal cavity 104 with an expanded section 106. Elastomeric insert 108 is received in the expanded section 106 and has a forwardly disposed conical face 110, best seen in FIG. 13. Conical face 110 is split along at least three lines 112 to form three "petals" 113, but optionally could be split along four or more lines. The split face permits passage of a catheter C, as shown in broken line in FIG. 12. Passage of the catheter C causes the petals defined in the face 110 to open to permit passage of the catheter, as illustrated in broken line in FIG. 12. When the catheter C is removed, the petals of face 110 will close, and will remain sealed when exposed to positive pressure in the cavity 104. The elastomeric insert 108 may further include an annular ring 114 disposed distally of the forward face 110. The annular ring contributes to the hoop strength in the insert. In some cases, ring 114 may further provide for a sliding seal against the catheter when passing through the insert.

Although the foregoing invention has been described in some detail by way of illustration and example, for purposes of clarity of understanding, it will be obvious that certain changes and modifications may be practiced within the scope of the appended claims.

What is claimed is:

1. An aortic introducer catheter for use with an obturator having a proximal end, a distal portion, and a deflecting mechanism actuable from the proximal end of the obturator for laterally deflecting at least the distal portion, the aortic introducer catheter comprising:

a flexible sheath having a proximal end, a distal end, and a lumen extending therebetween for removably receiving the obturator, wherein the length between the proximal and distal ends is in the range from 30 cm to 60 cm and the lumen diameter is in the range from 5 mm to 10 mm; and a hemostasis valve secured to the proximal end of the sheath;

wherein the distal end of the sheath is sufficiently flexible so as to be laterally deflectable by the deflecting mechanism of the obturator when the obturator is within the lumen of the sheath, so that the obturator can steer the sheath within a tortuous blood vessel, and wherein the flexible sheath comprises:

a tubular inner liner having a proximal end, a distal end, and a lumen therebetween;

a flat wire helical coil wrapped over an exterior surface of the tubular inner liner, said coil having spaced-apart adjacent turns; and a plastic coating formed over the helical coil, penetrating into the space between adjacent turns of the coil, and bonded to the tubular inner liner.

2. An aortic introducer catheter for use with an obturator having a proximal end, a distal portion, and a deflecting mechanism actuable from the proximal end of the obturator for laterally deflecting at least the distal portion, the aortic introducer catheter comprising:

a flexible sheath having a proximal end, a distal end, and a lumen extending therebetween for removably receiving the obturator, wherein the length between the proximal and distal ends is in the range from 30 cm to 60 cm and the lumen diameter is in the range from 5 mm to 10 mm, and a hemostasis valve secured to the proximal end of the sheath;

wherein the distal end of the sheath is sufficiently flexible so as to be laterally deflectable by the deflecting mechanism of the obturator when the obturator is within the lumen of the sheath, so that the obturator can steer the sheath within a tortuous blood vessel, and wherein the hemostasis valve comprises:

a housing having an interior and axially aligned inlet and outlet ports; and a compressible insert disposed within the interior of the housing, said insert including a polymeric foam body having an open axial lumen and an exterior geometry which is similar to but larger than the cavity in the housing, wherein the insert is confined within the cavity to close the lumen with said closed lumen being aligned between the inlet and outlet ports.

3. A catheter sheath for use with an obturator having a proximal end, a distal portion, and a deflecting mechanism actuable from the proximal end of the obturator for laterally deflecting at least the distal portion, the sheath comprising:

a tubular inner liner having a proximal end, a distal end, and a lumen therebetween for removably receiving the obturator, the distal end having a region of enhanced flexibility;

a flat wire helical coil wrapped over an exterior surface of the tubular inner liner, said coil having consistently spaced-apart adjacent turns; and a plastic coating formed over the helical coil, penetrating into the space between adjacent turns of the coil, and bonded to the tubular inner liner;

wherein the distal end of the sheath is laterally deflectable by the deflecting mechanism of the obturator when the obturator is within the lumen of the sheath.

4. A catheter sheath as in claim 3, wherein the tubular liner is composed of a material selected from the group consisting of polyurethane, polytetrafluoroethylene, fluorinated ethylene-propylene polymer, polyether block amide copolymer, polyamide, and polyethylene and has a wall thickness in the range from 0.08 mm to 0.15 mm.

5. A catheter sheath as in claim 3, wherein the helical coil comprises a stainless steel ribbon having a width in the range from 0.5 mm to 1.5 mm and thickness in the range from 0.08 mm to 0.15 mm, wherein the ribbon is wrapped at from 5 turns to 15 turns per cm and wherein the spacing between adjacent turns is in the range from 0.5 mm to 1 mm.

6. A catheter sheath as in claim 3, wherein the plastic coating is composed of a material selected from the group consisting of polyurethane, polyether block amide copolymer, polyethylene, and polyamide, and has a thickness measured from tubular inner liner in the range from 0.08 mm to 0.15 mm.

7. A catheter sheath as in claim 3; having a region of enhanced flexibility over a distal length in the range from about 5 cm to 15 cm.

8. A catheter sheath as in claim 3, having a soft tip free from the helical coil over a distal length in the range of 2 mm to 10 mm.

9. A catheter sheath as in claim 3, further comprising a hemostasis valve secured to the proximal end of the sheath.

10. A catheter sheath as in claim 3, wherein the lumen diameter is in the range from 5 mm to 10 mm, and wherein the region of enhanced flexibility accepts a 1 cm radius curve without kinking or collapse of the lumen.

11. A steerable obturator for use with a flexible catheter sheath having a proximal end, a distal end, and a lumen extending therebetween, said obturator comprising:

a flexible body having a proximal end and tapered distal tip, the flexible body removably receivable in the lumen of the sheath; and a deflecting mechanism actuable from the proximal end of the flexible body for laterally deflecting at least a distal portion of the flexible body;

wherein the distal portion of the flexible body is capable of redirecting axial advancement of the sheath by actuating the deflecting mechanism while the sheath advances distally over the obturator.

12. A steerable obturator as in claim 11, wherein the deflecting mechanism can induce a bend in a catheter body having a length in the range from 45 cm to 60 cm and an outer diameter in the range from 4 mm to 5 mm by laterally deflecting the distal portion within the lumen.

13. A steerable obturator as in claim 12, wherein the flexible body has a region of enhanced flexibility over a distal length in the range from about 5 cm to 10 cm.

14. A steerable obturator as in claim 13, wherein the region of enhanced flexibility comprises an axial series of elements connected by pivoting joints.

15. A steerable obturator as in claim 11, wherein the deflecting means comprises a pull wire attached off center at the distal end of the flexible body.

16. A steerable obturator as in claim 15, wherein the deflecting means further comprises a handle assembly attached to the proximal end of the flexible body, wherein said handle assembly includes a first portion attached to the pull wire and a second portion attached to the flexible body, whereby relative movement of the two portions causes lateral deflection of the distal portion.

17. A steerable obturator as in claim 11, wherein the deflecting mechanism of the obturator induces a deflection with a 1 cm radius in the sheath.

18. A steerable obturator as in claim 11, wherein the obturator has an outer diameter which is at least 75% of an inner diameter of the sheath.

19. A hemostasis valve for use with a catheter having an outer surface, the hemostasis valve comprising:

a housing having an interior cavity and axially aligned inlet and outlet ports;

an elastomeric insert within the interior cavity of the housing, said insert having a forwardly disposed conical face, wherein the face is radially split to permit passage of a catheter therethrough and an annular ring disposed proximally of the face, the annular ring having an open lumen which is adapted to form a sliding seal with the outer surface of the catheter.

20. A hemostasis valve as in claim 19, wherein the annular ring is formed integrally with the insert.

21. A hemostasis valve as in claim 19, wherein the face is radially split along at least three lines.

22. A hemostasis valve as in claim 19, wherein the lumen is coated with a lubricant.

23. A hemostasis valve as in claim 22, wherein the lubricant is selected from the group consisting of polyurethane and silicone.

24. A hemostasis valve as in claim 19, wherein the housing adjacent the ring is fixed.

* * * * *